(12) United States Patent
Bein et al.

(10) Patent No.: US 6,667,388 B2
(45) Date of Patent: Dec. 23, 2003

(54) PEPTIDE INHIBITOR OF MMP ACTIVITY AND ANGIOGENESIS

(75) Inventors: Kiflai Bein, Boston, MA (US); Michael Simons, Chestnut Hill, MA (US)

(73) Assignee: Beth Israel Deaconess Medical Center, Boston, MA (US)

( * ) Notice: Subject to any disclaimer, the term of this patent is extended or adjusted under 35 U.S.C. 154(b) by 0 days.

(21) Appl. No.: 09/766,700

(22) Filed: Jan. 22, 2001

(65) Prior Publication Data

US 2002/0159989 A1 Oct. 31, 2002

(51) Int. Cl.$^7$ ............................................. A61K 38/00
(52) U.S. Cl. ....................................... 530/300; 530/323
(58) Field of Search .................................. 530/300, 323

(56) References Cited

PUBLICATIONS

Burgess et al., J of Cell Bio. 111:2129–2138, 1990.*
Lazar et al. Molecular and Cellular Biology 8:1247–1252, 1988.*
Bowie et al. Science, 247:1306–1310, 1990, p. 1306, col. 2.*
Kuhn et al.(SwissProt. Database, Accession No. Q01644, Mech. Dev. vol. 35, 1991).*
Bein et al., "Thrombospondin Type 1 Repeats Interact with Matrix Metalloproteinase 2," The Journal of Biological Chemistry, vol. 275, No. 41, Oct. 13, pp 32167–32173, (2000).
Marra et al., "GenBank Accession No. AA103010: mo16e09.r1 Life Tech Mouse embryo 13 5dpc 1066014 Mus musculus cDNA clone IMAGE: 553768 5', mRNA sequence." Retrieved on Mar. 7, 2001.
Marra, et al., "GenBank Accession No. AA638088: vr22h10.r1 Barstead mouse myotubes MPLRB5 Mus musculus cDNA clone IMAGE: 1121443 5', mRNA sequence." Retrieved on Mar. 7, 2001.
Marra et al., "GenBank Accession No. AA711904: vu28h08.r1 Barstead mouse myotubes MPLRB5 Mus musculus cDNA clone IMAGE: 1182015 5', mRNA sequence." Retrieved on Mar. 7, 2001.
Marra et al., "GenBank Accession No. AA792844: vs89f04.r1 Barstead mouse myotubes MPLRB5 Mus musculus cDNA clone IMAGE: 1153471 5', mRNA sequence." Retrieved on Mar. 7, 2001.
Marra et al. "GenBank Accession No. AI115802: ue95e09.y1 Sugano mouse embryo mewa Mus musculus cDNA clone IMAGE: 1498888 5', mRNA sequence." Retrieved on Mar. 7, 2001.
Marra et al., "GenBank Accession No. AI593811: vr22h10.y1 Barstead mouse myotubes MPLRB5 Mus musculus cDNA clone IMAGE:1121443 5', mRNA sequence." Retrieved on Mar. 7, 2001.
Hayashizaki, et al., "GenBank Accession No. AK004732: Mus musculus adult male lung cDNA, RIKEN full–length enriched library, clone: 1200013A08, full insert sequence." Retrieved on Mar. 7, 2001.
Hayashizaki, et al. "GenBank Accession No. BB582376: BB582376 RIKEN full–length enriched, adult make colon Mus musculus cDNA clone 9030402I05 5', mRNA sequence." Retrieved on Mar. 7, 2001.
Hayashizaki, et al. "GenBank Accession No. BB585858: RIKEN full–length enriched, adult male urinary bladder Mus musculus cDNA clone 9530001E13 5', mRNA sequence." Retrieved on Mar. 7, 2001.
Chin, H., "GenBank Accession No. BE861182: UI–M–AM0–adv–f–04–0–UI.r1 NIH_BMAP_MAM Mus musculus cDNA clone UI–M–AM0–adv–f–04–0–UI 5', mRNA sequence." Retrieved on Mar. 7, 2001.
Strausberg, R., "GenBank Accession No. BF786652: 602111409F1NCI_CGAP_Kid14 Mus musculus cDNA clone IMAGE: 4239626 5', mRNA sequence." Retrieved on Mar. 7, 2001.
Strausberg, R. "GenBank Accession No. BF788855: 602110567F2 NCI_CGAP_Kid14 Mus Musculus cDNA clone IMAGE: 4238608 5', mRNA sequence." Retrieved on Mar. 7, 2001.
Kiflai Bein. "Thrombospondins 1 and 2 Inhibit Activation of Pro–Metalloproteinases 2 and 9 Enzymes:" Supplement II, Circulation, vol. 102, No 18, pp. II.174, Oct. 31, 2000.
Good, D.J., et al., "A Tumor Suppressor–dependent Inhibitor of Angiogenesis is Immunologically and Fuctionally Indistinguishble from a Fragment of Thrombospondin", Proc. Natl. Acad. Sci. USA, vol. 87, pp. 6624–6628, Sep. 1990.
Streit, M., et al., "Thrombospondin–2: A Potent Endogenous Inhibitor of Tumor Growth and Angiogenesis" PNAS, vol. 96, No. 26, p. 14888–14893, Dec. 21, 1999.

* cited by examiner

Primary Examiner—Anthony C. Caputa
Assistant Examiner—Gary B. Nickol
(74) Attorney, Agent, or Firm—Testa, Hurwitz & Thibeault, LLP

(57) ABSTRACT

The present invention is directed to peptides that interacts with thrombospondin 2 and inhibit matrix metalloproteinase 9 (MMP-9) activity. Consequently, the invention provides peptides that inhibit MMP-9 activity and are useful as inhibitors of angiogenesis and metastasis, among other diseases regulated by MMP-9. The peptides of the invention and their methods of use are therapeutic against diseases, such as cancer and arthritis, which are characterized by neovascularization.

3 Claims, 3 Drawing Sheets

US 6,667,388 B2

SEQUENCE LISTING

```
<160> NUMBER OF SEQ ID NOS: 8

<210> SEQ ID NO 1
<211> LENGTH: 26
<212> TYPE: PRT
<213> ORGANISM: Artificial Sequence
<220> FEATURE:
<223> OTHER INFORMATION: Peptide Inhibitor of MMP-9 Activity and
      Angiogenesis

<400> SEQUENCE: 1

Ala Pro Trp Asn Cys Cys Pro Val Ser Cys Cys Gly Asn Cys Cys Phe
1               5                   10                  15

Phe Arg Ala Leu Gln Ser Cys Pro Gln Gly
            20                  25

<210> SEQ ID NO 2
<211> LENGTH: 78
<212> TYPE: DNA
<213> ORGANISM: Artificial Sequence
<220> FEATURE:
<223> OTHER INFORMATION: Nucleic Acid encoding peptide of SEQ ID NO.1

<400> SEQUENCE: 2
gcgccatgga actgctgtcc cgtgtcctgc tgtggaaact gctgcttctt cagagctctg         60
cagtcctgtc ctcaggga                                                      78

<210> SEQ ID NO 3
<211> LENGTH: 30
<212> TYPE: DNA
<213> ORGANISM: Artificial Sequence
<220> FEATURE:
<223> OTHER INFORMATION: Mouse TSP1-TSR sense PCR primer

<400> SEQUENCE: 3
ggaattccat atggctgacg atggctggtc                                          30

<210> SEQ ID NO 4
<211> LENGTH: 33
<212> TYPE: DNA
<213> ORGANISM: Artificial Sequence
<220> FEATURE:
<223> OTHER INFORMATION: Mouse TSP1-TSR reverse PCR primer

<400> SEQUENCE: 4
ccgctcgagc tcatccatca attgggcagt cct                                      33
```

```
<210> SEQ ID NO 5
<211> LENGTH: 27
<212> TYPE: DNA
<213> ORGANISM: Artificial Sequence
<220> FEATURE:
<223> OTHER INFORMATION: Mouse TSP2-TSR sense PCR primer

<400> SEQUENCE: 5
tcccccgggg tgaggctggt ctccgtg                                    27

<210> SEQ ID NO 6
<211> LENGTH: 27
<212> TYPE: DNA
<213> ORGANISM: Artificial Sequence
<220> FEATURE:
<223> OTHER INFORMATION: Mouse TSP2-TSR reverse PCR primer

<400> SEQUENCE: 6
gctctagatc acccatcata ggcagct                                    27

<210> SEQ ID NO 7
<211> LENGTH: 9
<212> TYPE: PRT
<213> ORGANISM: Artificial Sequence
<220> FEATURE:
<223> OTHER INFORMATION: HA tag

<400> SEQUENCE: 7

Tyr Pro Tyr Asp Val Pro Asp Tyr Ala
 1               5

<210> SEQ ID NO 8
<211> LENGTH: 8
<212> TYPE: PRT
<213> ORGANISM: Artificial Sequence
<220> FEATURE:
<223> OTHER INFORMATION: Flag tag

<400> SEQUENCE: 8

Asp Tyr Lys Asp Asp Asp Asp Lys
 1               5
```

PEPTIDE INHIBITOR OF MMP ACTIVITY AND ANGIOGENESIS

GOVERNMENT SUPPORT

Work described herein was supported in part by a grant from the National Institutes of Health, NIH HL 53793. The government may have certain rights in the invention.

FIELD OF THE INVENTION

The present invention is directed to peptide inhibitors of angiogenesis. More specifically, this invention relates to a peptide that interacts with thrombospondin 2 and inhibits matrix metalloproteinase 9 (MMP-9) activity.

BACKGROUND OF THE INVENTION

Matrix metalloproteinases, or MMPs, are a family of zinc proteinases that digest the extracellular matrix and are implicated in a variety of pathological conditions, including early stages of angiogenesis, cardiovascular diseases, and cancer metastasis. Compounds that inhibit MMP activity are thought to be useful for the treatment or prophylaxis of conditions that involve tissue breakdown. These include rheumatoid arthritis, osteoarthritis, gastric ulceration, cancer metastasis as well as management of angiogenesis-dependent diseases. There is growing body of evidence suggesting that anti-angiogenic inhibitors will improve future therapies of diseases such as cancer, rheumatoid arthritis and ocular neovascularization. Important therapeutic strategies include suppression of activity of the major angiogenic regulators such as vascular endothelial growth factor (VEGF) and fibroblast growth factor (FGF); inhibition of activity of alphav-integrins and matrix metalloproteinases (MMPs); and the exploitation of endogenous anti-angiogenic molecules like angiostatin, endostatin or thrombospond.

Matrix metalloproteinases or MMPs, including MMP-2 and MMP-9, are expressed in a variety of tissues. Matrix metalloproteinase 9 degrades Type IV collagen, a major component of extracellular matrix and is believed to be crucial for cancer invasion, metastasis and angiogenesis.

Angiogenesis is the process of new blood vessel development and formation and plays an important role in numerous physiological events, both normal and pathological. Angiogenesis occurs in response to specific signals and involves a complex process characterized by infiltration of the basal lamina by vascular endothelial cells in response to angiogenic growth signal(s), migration of the endothelial cells toward the source of the signal(s), and subsequent proliferation and formation of the capillary tube. Blood flow through the newly formed capillary is initiated after the endothelial cells come into contact and connect with a preexisting capillary. Unregulated angiogenesis becomes pathologic and sustains progression of many neoplastic and non-neoplastic diseases. A number of serious diseases are dominated by abnormal neovascularization, including solid tumor growth and metastases, arthritis, some types of eye disorders, and psoriasis. See, e.g., reviews by Moses et al., 1991, Biotech. 9:630–634; Folkman et al., 1995, N. Engl. J. Med., 333:1757–1763; Auerbach et al., 1985, J. Microvasc. Res. 29:401–411; Folkman, 1985, Advances in Cancer Research, eds. Klein and Weinhouse, Academic Press, New York, pp. 175–203; Patz, 1982, Am. J. Opthalmol. 94:715–743; and Folkman et al., 1983, Science 221:719–725.

In a number of pathological conditions, the process of angiogenesis contributes to the disease state. For example, significant data have accumulated which suggests that the growth of solid tumors and lethality are dependent on angiogenesis. Folkman and Klagsbrun, 1987, Science 235:442–447. The naturally occurring balance between endogenous stimulators and inhibitors of angiogenesis is one in which inhibitory influences predominate. Rastinejad et al., 1989, Cell 56:345–355. In those rare instances in which neovascularization occurs under normal physiological conditions, such as wound healing, organ regeneration, embryonic development, and female reproductive processes, angiogenesis is stringently regulated and spatially and temporally delimited. Under conditions of pathological angiogenesis such as those characterizing solid tumor growth, these regulatory controls fail.

Thrombospondins are naturally occurring inhibitors of angiogenesis. However, the molecular mechanisms by which they function are not well understood. Thrombospondins (TSP) are a family of extracellular matrix glycoproteins that include at least five related members (TSP 1–5). Thrombospondins are thought to play a role in a number of biological processes including coagulation, cell adhesion, cell growth, modulation of cell—cell and cell-matrix interactions, control of tumor growth and metastases, and angiogenesis. Thrombospondin-1 (TSP-1) is the most extensively studied thrombospondin to date. TSP-1 is capable of inhibiting neovascularization induced by angiogenic factors. In addition, TSP-1 has been shown to inhibit angiogenesis both in vitro and in vivo. The role of Thrombospondin-2 (TSP-2) in angiogenesis, however, is not very well understood.

Thrombospondin-1 and Thrombospondin-2 share many structural properties. Both contain N- and C-terminal globular domains flanking a procollagen homology region, three properdin-like type 1 repeats (TSR), three EGF-like type 2 repeats and seven Ca2+ binding type 3 repeats. Structure-function studies have localized the anti-angiogenic region of TSP-1 to the procollagen-like region and the TSR. Thrombospondin-1 and Thrombospondin-2 share a high degree of homology in the TSR region. The spatial and temporal expression of TSP-1 and TSP-2 is very different both during embryonic development and in adult tissues. However similar to TSP-1, TSP-2 is highly expressed in developing blood vessels. Previously, it was reported that the TSR domains of both TSP-1 and TSP-2 interact with the N-terminal region of MMP-2, resulting in the inhibition of MMP catalytic activity. Although, both TSP-1 and TSP-2 are thought to elicit anti-angiogenic properties, TSP-1 and TSP-2 knockout mice exhibit different phenotypes suggesting different mechanisms of action. TSP-1 knockout mice show abnormalities primarily in the lungs with an increase in neutrophils and macrophages, suggestive of diffuse alveolar hemorrhage. The lack of TSP-2 expression in the presence of normal levels of TSP-1 expression is associated with disordered collagen fibrillogenesis and an increase in blood vessel count in the skin and other tissues. Furthermore, the tsp-2$^{-/-}$ mice demonstrated accelerated angiogenesis. These and other changes are consistent with increased MMP activity. Although, the tsp-2$^{-/-}$ mice show phenotypic changes that are consistent with increased MMP activity, the mechanism(s) by which TSP-2 inhibits MMP activity are not known. Understanding the mechanisms underlying the anti-angiogenic properties of TSP will aid in the exploitation of these molecules in the treatment of various angiogenesis related diseases and potentially diseases that show increased MMP activity.

SUMMARY OF THE INVENTION

This invention provides peptides that inhibit MMP-9 and are useful as inhibitors of angiogenesis and metastasis, among other activities regulated by MMP-9. More specifically, the present invention provides peptides that interact with the TSR domain of thrombospondins, especially TSP-2, and inhibit MMP-9 activity. As a consequence, peptides of the invention, and their methods of use, are therapeutics against diseases, such as cancer and arthritis, which are characterized by neovascularization and tissue break down.

The invention provides a link between thrombospondins and matrix metalloproteinases and is based upon the discovery of a novel class of peptide inhibitors of MMP-9. Inhibitory peptides of the invention bind to the TSR domain of thrombospondins and cause a reduction in MMP-9 activation and its attendant effects on angiogenesis. Exemplary of this class of peptides is the peptide shown in SEQ ID NO:1. According to the invention, this peptide binds to the TSR domain of TSP-2 and inhibits MMP-9 activity. The invention also provides analogs, homologs and fragments of the peptide shown in SEQ ID NO:1 (APWNCCPVSCCGNCCFFRAL QSCPQG) which maintain the ability to bind to TSP-2 and to inhibit MMP-9 activity. The invention further provides nucleic acids encoding the peptides described above. In particular, in a preferred embodiment, a nucleic acid of the invention is shown in SEQ ID NO:2 (5' GCGCC ATGGAACTGCTGTCCCGT-GTCCTGCTGTGGAAACTGCTGCTTCT-TCAGAGCTCTGCAGTC CTGTCCTCAGGGA).

The invention also comprises antibodies to epitope(s) encoded by the peptide or fragments of the peptide in SEQ ID NO:1. These antibodies are either polyclonal or monoclonal. The antibodies are made according to techniques known in the art.

This invention further comprises vectors containing the nucleic acid in SEQ ID NO:2 operably linked to regulatory DNA 5' or 3' of the nucleic acid of SEQ ID NO:2, that results in the translation of the nucleic acid into the peptide of SEQ ID NO:1. Regulatory DNA preferably comprises a promoter which is either a prokaryotic or a eukaryotic promoter, in order to facilitate expression in prokaryotic and eukaryotic cells respectively. In addition, vectors may contain the nucleic acid in SEQ ID NO:2 linked in-frame to another piece of DNA which results in expression of a fusion protein containing the peptide in SEQ ID NO:1 or homologs, fragments and variants of the peptide of this invention.

A preferred embodiment of the invention is a prokaryotic cell carrying the nucleic acid in SEQ ID NO:2 expressing the peptide in SEQ ID NO:1 or a fragment or variant or homolog that retains the MMP-9 inhibitory activity; a vector expressing the peptide or a fusion protein containing the peptide in SEQ ID NO:1 or a fragment or variant or homolog of the peptide.

Another preferred embodiment of the invention is a eukaryotic cell carrying the nucleic acid in SEQ ID NO:2 expressing the peptide in SEQ ID NO:1 or a fragment or variant or homolog that retains the MMP-9 inhibitory activity; a vector expressing the peptide or a fusion protein containing the peptide in SEQ ID NO:1 or a fragment or variant or homolog of the peptide.

Pharmaceutical compositions of peptide or fragments, variants or homologs of the peptide may be used to inhibit the action of MMP-9, for example, in the treatment or prophylaxis of disorders characterized by degradation of the extracellular matrix, such as, for example, cancer, arthritis and, cardiovascular disorders. Compositions of the invention are provided to an animal by any suitable means, directly (e.g., locally, as by injection, implantation or topical administration to a tissue locus) or systemically (e.g., parenterally or orally). Where the compositions of the invention are to be provided parenterally, such as by intravenous, subcutaneous, opthalmic, intraperitoneal, intramuscular, buccal, rectal, vaginal, intraorbital, intracerebral, intracranial, intraspinal, intraventricular, intrathecal, intracisternal, intracapsular, intranasal or by aerosol administration, the composition preferably comprises part of an aqueous or physiologically compatible fluid suspension or solution.

BRIEF DESCRIPTION OF THE FIGURES

FIG. 2 further shows the inhibitory effect of the peptide of the invention on MMP-9 activity, for example, the chart shows the effects of MBP fused with the catalytic domain of MMP3, MBP fused with the hemopexin domain of MMP3, and MBP fused with GenBank Accession AA711904, Barstead mouse mytotubes MPLRB5.

DETAILED DESCRIPTION OF THE PREFERRED EMBODIMENTS

Figure 1:
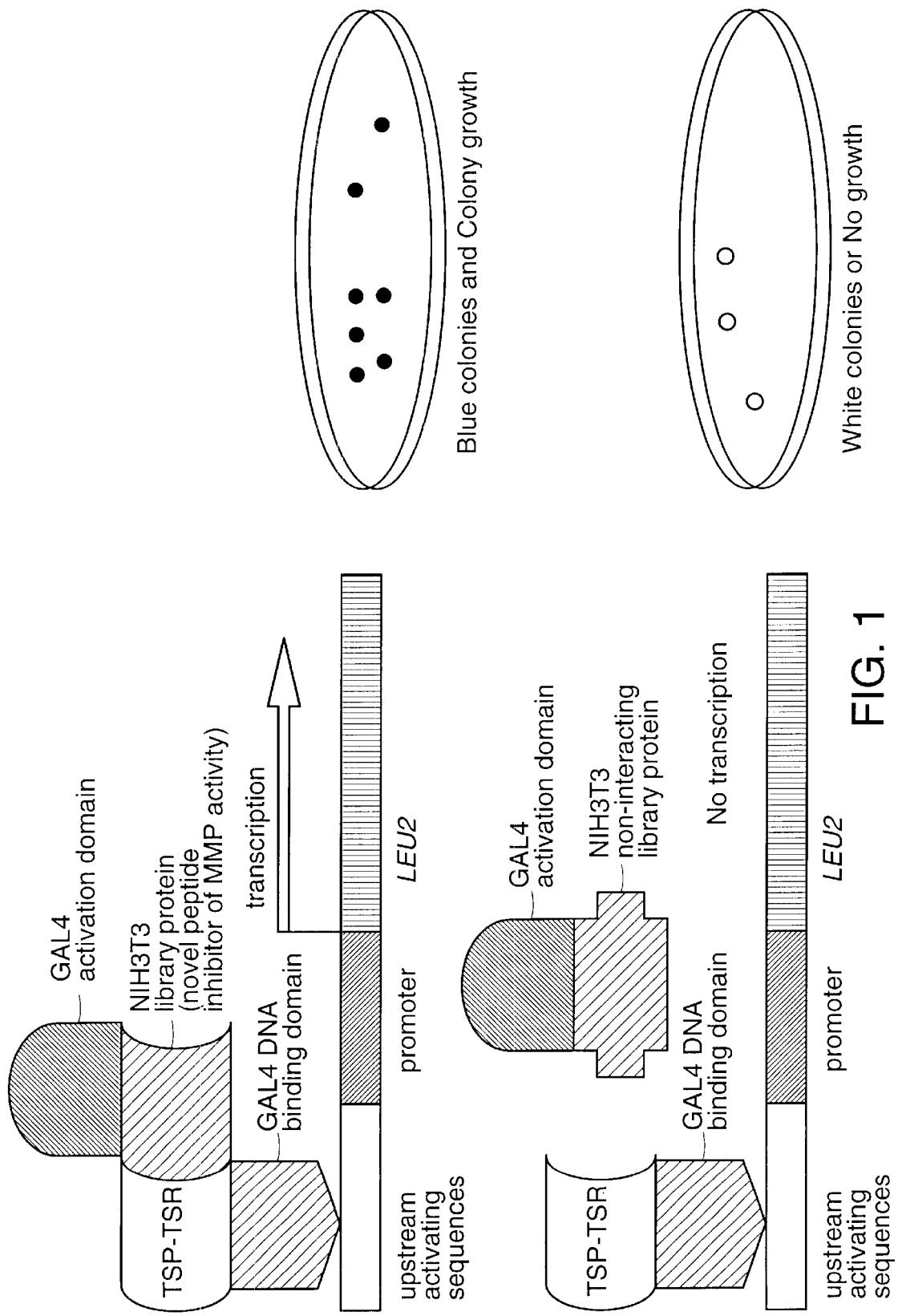
FIG. 1: is a schematic of the yeast-two hybrid system used for the isolation of the cDNA encoding the peptide of the invention in SEQ ID NO:1.

The present invention provides a peptide of SEQ ID NO:1 that interacts with thrombospondin-2 and inhibits MMP-9 activity. As used herein, a homolog, fragment or variant of the peptide is defined by its ability to inhibit MMP-9 activity. MMP-9 activity can be measured by the assay described herein or by other assays available in the art. The present invention also provides a nucleic acid, in SEQ ID NO:2, that encodes the peptide in SEQ ID NO:1. A nucleic acid according to the invention may be genomic DNA or cDNA. In the case in which a nucleic acid is transcribed and translated to produce a functional peptide, defined in this case as a peptide that retains MMP-9 inhibitory activity, one of skill in the art recognizes that because of codon degeneracy a number of different nucleic acids encode the same peptide. In addition, the invention includes those peptides, referred to as variants of the peptide in SEQ ID NO:1, that have amino acid sequence substantially identical (as described below) with the peptide in SEQ ID NO:1 and inhibit MMP 9 activity. Variants include peptides with conserved amino acid changes in the sequence of SEQ ID NO:1. Conserved amino acid substitutions are those changes that can be made without altering the function of the native peptide in SEQ ID NO:1.

Homologs of the peptide in SEQ ID NO:1 are peptides that are "substantially identical" to the peptide in SEQ ID NO:1, retain the MMP-9 inhibitory activity and are found in or isolated from different species of animals than the peptide in the present invention, which is murine in origin.

Homologs and variants of the peptide in SEQ ID NO:1 are defined by their ability to interact with TSP-2 and inhibit MMP-9 activity. The critical amino acids in a protein or peptide are those amino acids that are important for the function of the protein or peptide. These amino acids are often conserved across different species and organisms. It is well known to one skilled in the art that conserved amino acids are usually identical across species and organisms and if not, are very similar in their chemical properties. Homologs of the peptide in SEQ ID NO:1 are those peptides that are found in other species and organisms that inhibit MMP-9 activity. Homologs of the peptide in SEQ ID NO:1 will contain the conserved amino acids that are critical to the function of the peptide. These amino acids are either identical to the corresponding amino acids in SEQ ID NO:1 or have very similar chemical properties. Table I describes an amino acid substitution matrix that contains all possible exchanges of one amino acid with another. A low score of −4 signifies a low probability of substitution and a high score of 11 signifies a high probability of substitution. Henikoff, S and Henikoff, J. G, Proc. Natl. Acad. Sci. USA, 89: 10915–10919 (1992). Any amino acid substitution which has a high score according to this matrix will likely be a conserved amino acid change.

Variants of the peptide in SEQ ID NO:1, on the other hand, are those peptides that contain amino acid substitutions, wherein an amino acid can be replaced with another amino acid without altering the activity of the peptide. These amino acids may or may not be conserved across species and may or may not be essential to the MMP-9 inhibitory function of peptide.

two nucleic acids by taking into account codon degeneracy, amino acid similarity and reading frame positioning. Substantial identity of peptides for these purposes normally means sequence identity of at least [40%], preferably at least [60%], more preferably at least [90%], and most preferably at least [95%] identical to all or a portion of a reference peptide.

In a preferred embodiment, the invention comprises any nucleic acid with at least 97% identity to the nucleic acid in SEQ ID NO:2.

Peptides of the invention inhibits both the basal activity of proMMP-9 as well as that of activated MMP-9.

Peptides of the invention or homologs are isolated and characterized as interactors of TSP-2 that inhibit MMP-9 activity. The peptides of the invention can be synthesized by methods well known in the art or isolated from cells or tissues of organisms that express high levels of the mRNA for the peptide. mRNA is isolated from the appropriate cell or tissue using standard methods known in the art and reverse transcribed to generate the corresponding DNA. The DNA is subsequently transcribed and translated into the corresponding peptide.

Nucleic acids encoding peptides of the invention are cloned in either prokaryotic or eukaryotic expression vectors by standard cloning techniques known in the art. The expression vectors are transformed or transfected, depending on the host cell, into an appropriate cell by methods well

TABLE 1

|   | A | R | N | D | C | Q | E | G | H | I | L | K | M | F | P | S | T | W | Y | V |
|---|---|---|---|---|---|---|---|---|---|---|---|---|---|---|---|---|---|---|---|---|
| A | 4 | -1 | -2 | -2 | 0 | -1 | -1 | 0 | -2 | -1 | -1 | -1 | -1 | -2 | -1 | 1 | 0 | -3 | -2 | 0 |
| R | -1 | 5 | 0 | -2 | -3 | 1 | 0 | -2 | 0 | -3 | -2 | 2 | -1 | -3 | -2 | -1 | -1 | -3 | -2 | -3 |
| N | -2 | 0 | 6 | 1 | -3 | 0 | 0 | 0 | 1 | -3 | -3 | 0 | -2 | -3 | -2 | 1 | 0 | -4 | -2 | -3 |
| D | -2 | -2 | 1 | 6 | -3 | 0 | 2 | -1 | -1 | -3 | -4 | -1 | -3 | -3 | -1 | 0 | -1 | -4 | -3 | -3 |
| C | 0 | -3 | -3 | -3 | 9 | -3 | -4 | -3 | -3 | -1 | -1 | -3 | -1 | -2 | -3 | -1 | -1 | -2 | -2 | -1 |
| Q | -1 | 1 | 0 | 0 | -3 | 5 | 2 | -2 | 0 | -3 | -2 | 1 | 0 | -3 | -1 | 0 | -1 | -2 | -1 | -2 |
| E | -1 | 0 | 0 | 2 | -4 | 2 | 5 | -2 | 0 | -3 | -3 | 1 | -2 | -3 | -1 | 0 | -1 | -3 | -2 | -2 |
| G | 0 | -2 | 0 | -1 | -3 | -2 | -2 | 6 | -2 | -4 | -4 | -2 | -3 | -3 | -2 | 0 | -2 | -2 | -3 | -3 |
| H | -2 | 0 | 1 | -1 | -3 | 0 | 0 | -2 | 8 | -3 | -3 | -1 | -2 | -1 | -2 | -1 | -2 | -2 | 2 | -3 |
| I | -1 | -3 | -3 | -3 | -1 | -3 | -3 | -4 | -3 | 4 | 2 | -3 | 1 | 0 | -3 | -2 | -1 | -3 | -1 | 3 |
| L | -1 | -2 | -3 | -4 | -1 | -2 | -3 | -4 | -3 | 2 | 4 | -2 | 2 | 0 | -3 | -2 | -1 | -2 | -1 | 1 |
| K | -1 | 2 | 0 | -1 | -3 | 1 | 1 | -2 | -1 | -3 | -2 | 5 | -1 | -3 | -1 | 0 | -1 | -3 | -2 | -2 |
| M | -1 | -1 | -2 | -3 | -1 | 0 | -2 | -3 | -2 | 1 | 2 | -1 | 5 | 0 | -2 | -1 | -1 | -1 | -1 | -1 |
| F | -2 | -3 | -3 | -3 | -2 | -3 | -3 | -3 | -1 | 0 | 0 | -3 | 0 | 6 | -4 | -2 | -2 | 1 | 3 | -1 |
| P | -1 | -2 | -2 | -1 | -3 | -1 | -1 | -2 | -2 | -3 | -3 | -1 | -2 | -4 | 7 | -1 | -1 | -4 | -3 | -2 |
| S | 1 | -1 | 1 | 0 | -1 | 0 | 0 | 0 | -1 | -2 | -2 | 0 | -1 | -2 | -1 | 4 | 1 | -3 | -2 | -2 |
| T | 0 | -1 | 0 | -1 | -1 | -1 | -1 | -2 | -2 | -1 | -1 | -1 | -1 | -2 | -1 | 1 | 5 | -2 | -2 | 0 |
| W | -3 | -3 | -4 | -4 | -2 | -2 | -3 | -2 | -2 | -3 | -2 | -3 | -1 | 1 | -4 | -3 | -2 | 11 | 2 | -3 |
| Y | -2 | -2 | -2 | -3 | -2 | -1 | -2 | -3 | 2 | -1 | -1 | -2 | -1 | 3 | -3 | -2 | -2 | 2 | 7 | -1 |
| V | 0 | -3 | -3 | -3 | -1 | -2 | -2 | -3 | -3 | 3 | 1 | -2 | 1 | -1 | -2 | -2 | 0 | -3 | -1 | 4 |

Optimal alignment of sequences for comparison is conducted by the homology algorithm of Needleman and Wunsch, J. Mol. Biol, 48: 443 (1970), by the search for similarity method of Pearson and Lipman, Proc. Natl. Acad. Sci. (U.S.A.) 85: 2444 (1988), by computerized implementations of algorithms in the Wisconsin Genetics Software Package, Genetics Computer Group (GCG), 575 Science Dr., Madison, Wis., or by visual inspection. The algorithms in GCG include GAP, BESTFIT, FASTA and TFASTA. The term "substantial identity" of a nucleic acid, peptide or protein means that the nucleic acid or peptide has at least [60%] sequence identity, preferably at least [80%], more preferably at least [90%] and most preferably at least [95%], compared to a reference nucleic acid or peptide using the programs described above. One of skill in the art recognizes that these values can be appropriately adjusted to determine corresponding identity of peptides or proteins encoded by known in the art. The peptide is expressed and subsequently isolated from the host cell expressing the peptide. The antibodies to the peptide or fragments thereof, which can be either monoclonal or polyclonal by nature, are used for the purification and isolation of the peptide.

The present invention is illustrated further by the following non-limiting examples. The peptide of the invention in SEQ ID NO: 1 was isolated as an interactor of TSP-2 using the yeast two-hybrid system. This is exemplary of a general approach for isolating the cDNA encoding the peptide of SEQ ID NO:1 and the cDNAs encoding the variants and homologs of the peptide.

I. Isolation of TSP2 Interacting Peptide:

Generally, the nomenclature and the laboratory procedures in recombinant DNA technology described here are well known to those skilled in the art and are commonly employed in the art. The peptide of SEQ ID NO:1 was isolated by the yeast two-hybrid system using the MATCHMAKER two-hybrid system from CLONTECH. See FIG. 1.

The *S. cerevisiae* strain Y190 (CLONTECH, CA) was used for cDNA library screening and for direct testing of protein—protein interactions. The cells were grown at 30° C. either in rich YPD media or minimal media with the appropriate amino-acid supplements. The minimal media were SD-Trp, in which tryptophan was omitted; SD-Leu, in which leucine was omitted; SD-Trp, Leu, in which both tryptophan and leucine were omitted, and SD-Trp, leu, His, in which tryptophan, leucne and histidine were lacking.

The constructs for use in the yeast two-hybrid system were based on the GAL4 two-hybrid system 2, which includes the cloning vectors pAS2-1 and pACT2 (CLONTECH, CA). The pAS2-1 vector carries the nutritional marker TRP1, for tryptophan, and allows the design of constructs, referred to as bait, for the expression of fusion proteins C-terminus of the GAL4(1–147) DNA binding domain. The pACT2 vector carries the nutritional marker LEU2, for leucine, and allows the design of constructs, referred to as prey, for the expression of fusion proteins C-terminus of the GAL4 (768–881) activation domain. A bait vector with a second reading frame, designated pAS2-2, was constructed by linearizing the pAS2-1 with NcoI and filling-in using $T_4$ DNA polymerase. The NIH3T3 activation cDNA library, constructed in the vector pACT2, was purchased from CLONTECH.

Mouse TSP-1-TSR was amplified by PCR using the sense primer which included an NdeI site,

5' GGAATTCCATATGGCTGACGATGGCTGGTC 3' (SEQ ID NO: 3)

and an antisense primer which contained an XhoI site,

5' CCGCTCGAGCTCATCCATCAATTGGGCAGTCCT 3' (SEQ ID NO: 4)

Similarly, mouse TSP2-TSR was amplified by PCR using the sense primer containing a SmaI site,

5' TCCCCCGGGGTGAGGCTGGTCTCCGTG 3' (SEQ ID NO: 5)

and an antisense primer containing an XbaI site,

5' GCTCTAGATCACCCATCATAGGCAGCT3' (SEQ ID NO: 6)

for subsequent cloning into the vectors pAS2-1 and pAS2-2, respectively.

The TSP-1 and TSP-2 TSR regions corresponded to nucleotides 1342–1861 and 1356–1876 of TSP-1 and TSP-2 respectively. The pAS2-2TSP2 type 1 construct was transformed into competent yeast strain Y190, selected on the appropriate medium and subsequently transformed with the pACT2 based NIH3T3 cDNA translational library. The Y190 cells were transformed using lithium acetate according to the instructions provided by CLONTECH. The pAS2 based constructs were selected on SD-Leu medium and the double transformants were selected on SD-Trp, Leu, His medium supplied with 45 mM 3-azo-1,2,4-triazole (3-AT).

During the screen, the interaction between the bait (TSP1-TSR or TSP2-TSR) and the prey (NIH3T3 translational library) were assessed by their ability to transactivate the reporter genes HIS3 and lacZ.

For the β-gal assay, the yeast colonies were lifted to filters that were subsequently submerged in liquid nitrogen for 10–20 seconds and thawed at room temperature. The membranes were incubated, colonies side up, at 30° C. on top of another membrane presoaked with Z-buffer (60 mM $Na_2HPO_4$, 10 mM KCl, 1 mM $MgSO_4$, pH 7.0, 50 mM β-mercaptoethanol) and 1 mg/ml X-gal. The positive clones were then screened with pAS2-1TSP1 type 1 construct to eliminate the clones that interact with TSP1-TSR. The plasmid DNA was rescued from colonies by cracking the cells in presence of glass-beads followed by purification using Geneclean glass milk beads (Bio101), subsequently leading to the isolation of the cDNA clone, as shown in SEQ ID NO:2, encoding the peptide in SEQ ID NO:1. The same approach is used to clone homologs of the peptide in SEQ ID NO:1 from other species.

The peptide of the invention may also be isolated from an organ, tissue or organism that expresses the mRNA for the peptide. The mRNA is subsequently reverse transcribed into DNA and cloned into an appropriate vector for translation into the peptide that has MMP-9 inhibitory function. The organ or tissue expressing the mRNA is identified by Northern blot analysis.

II. Isolation of RNA and Northern Blot Analysis:

Various organ tissue samples were collected from C57/B129 mice and subsequently quick frozen in liquid nitrogen. Total RNA was prepared using TriReagent solution (SIGMA). For Northern blot analysis, 15 μg of RNA was loaded per lane and fractionated on a 1.3% agarose-formaldehyde gel by electrophoresis. The RNA was transferred to GeneScreen Plus membrane (NEN Life Science Products) and hybridized using a random primed cDNA for the peptide isolated form the yeast two-hybrid screen. Hybridization was performed at 68° C. for 3 hours in Quickhyb solution (STRATAGENE). Following hybridization, filters were washed twice at room temperature in 2×SSC, 0.1% SDS for 5–10 minutes each and at 55 to 68° C. in 0.1% SSC, 0.1% SDS for 15–30 minutes and subjected to autoradiography. The highest level of transcript for the peptide in SEQ ID NO:1 was detected in lung tissue.

The nucleic acid of SEQ ID NO:2, as isolated from the yeast-two hybrid screen is used for the expression of the peptide or the peptide as a fusion protein either in vitro or in vivo III. Expression of the Peptide:

For expression in vitro, the peptide in SEQ ID NO:1 is expressed in the TNT® quick coupled transcription/translation system by PROMEGA. The cDNA in SEQ ID NO:2 is cloned into an appropriate vector either downstream of a T7 or SP6 promoter to be subsequently transcribed and translation.

The peptide is tagged with a tag such as HA or Flag, expressed in eukaryotic cells and subsequently purified on an affinity gel column using antibodies directed to the tag. The HA tag, a nonapeptide sequence of SEQ ID NO. 7 (YPYDVPDYA) of the hemagglutinin glycoprotein, and the flag, an octapeptide of SEQ ID NO. 8 (DYKDDDDK), are widely used in art for detecting and isolating recombinant proteins.

For expression of the peptide as a fusion protein for subsequent use in MMP-9 inhibition assays, the cDNA encoding the peptide in SEQ ID NO:2 was cloned into the prokaryotic expression vector pMAL.c2x (NEN). The peptide was expressed as a fusion with the maltose binding protein (MBP) in the bacterial strain, BL21-codon plus (STRATAGENE). The bacteria were transformed using any standard method known in the art and grown at 37° C., as recommended by the supplier. The bacterial culture was supplemented with IPTG (isopropyl B-D-thiogalacto pyranoside) to a final concentration of 0.3 mM and grown further. The fusion protein with MBP was subsequently extracted from the bacterial cells using purified amylose resin. ProMMP (CALBIOCHEM) was used for assessing functionality of the bacterially expressed MBP-fusion peptide.

The peptides of the invention are inhibitors of MMP-9 activity. The peptide of SEQ ID NO:1 was expressed as a fusion protein and tested in an in vitro assay for its ability to inhibit MMP-9 activity. The peptide of SEQ ID NO:1 was bacterially expressed as a fusion protein (MBP-peptide) and inhibited both the basal activity of proMMP-9 and that of proMMP-9 activated by MMP3. See FIG. 2 and FIG. 3.

Figure 2:
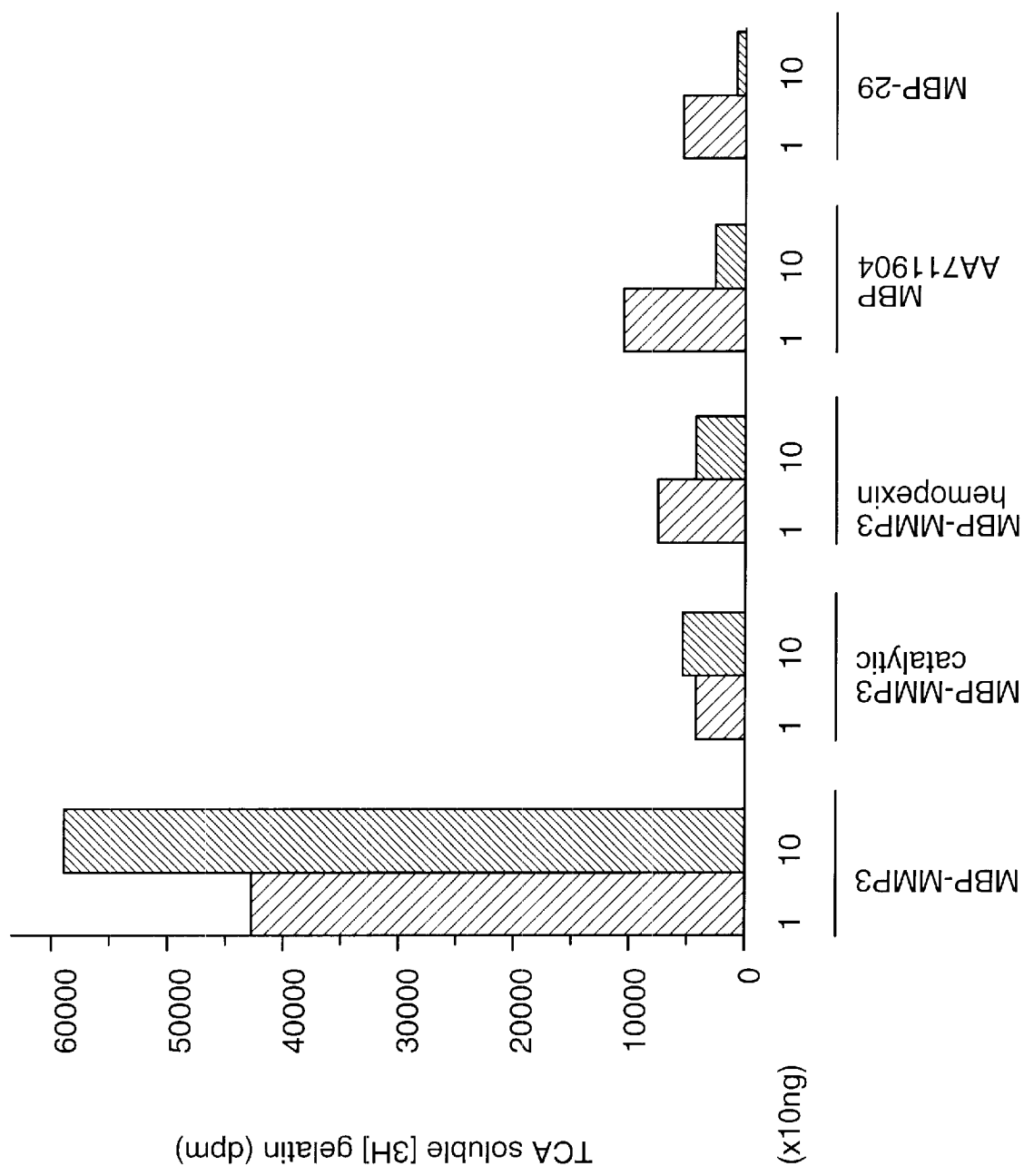
FIG. 2: is a bar graph depicting the inhibitory effect of the peptide of the invention on MMP-9 activity in an in vitro assay. ProMMP9 was preincubated at 37° C. for 2 hours with 10 or 100 ng of recombinant MBP-peptide fusion protein (MBP-29) followed by addition of [$^3$H]-labeled substrate for 1 hour.
Figure 3:
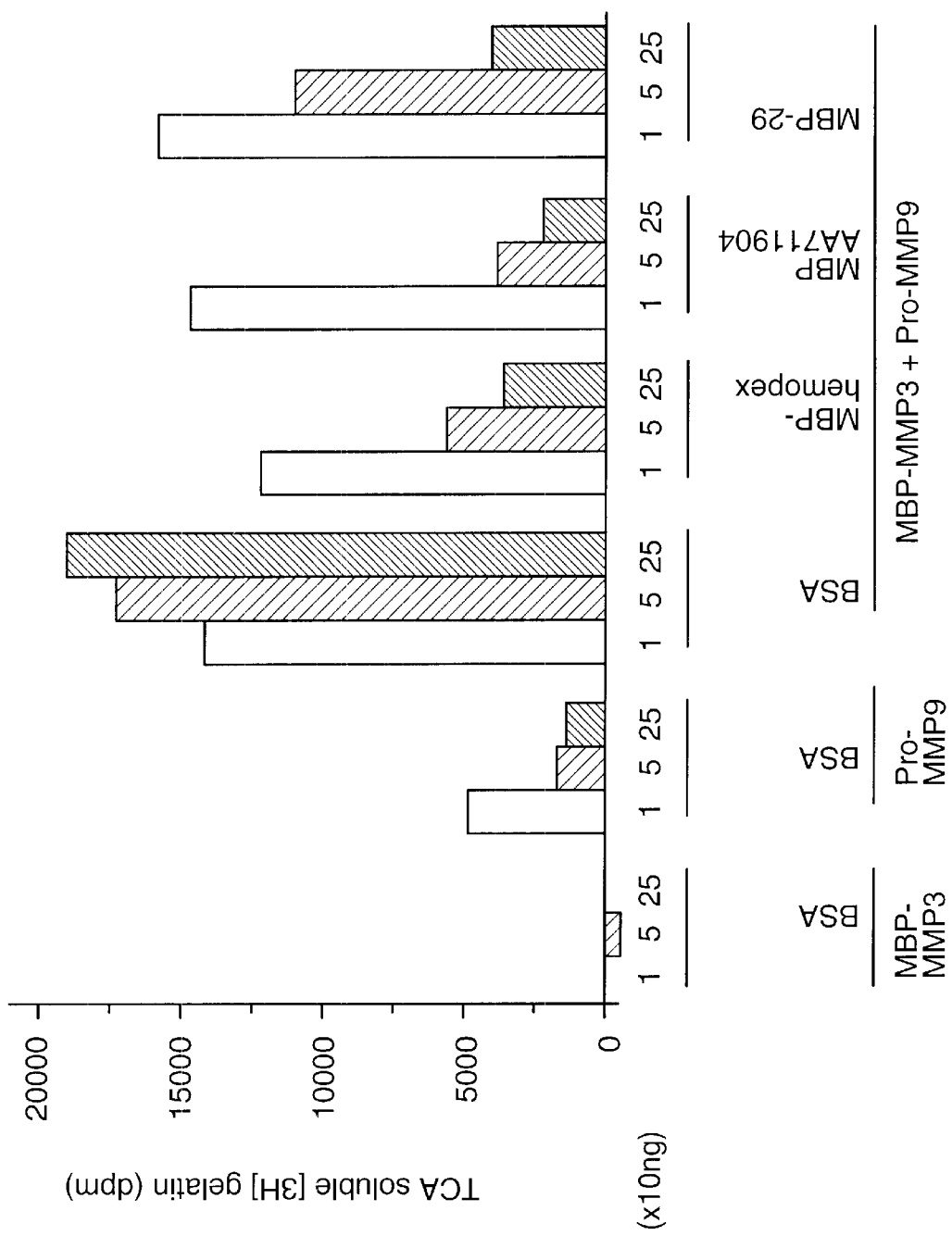
FIG. 3: is a bar graph depicting the inhibitory effect of the peptide of the invention on activated MMP-9 in an in vitro assay. ProMMP-9 activated with MBP-MMP3 was incubated for 2 hours with control protein or recombinant MBP-peptide fusion protein (MBP-29).

IV. Inhibition of MMP-9 Activity:

The enzymatic assays were performed using [3H]-labeled gelatin substrate. The MMP enzymatic assay buffer contained 50 mM Tris-HCl, pH 7.5 containing 5 mM $CaCl_2$, 200 mM NaCl, and 0.02% Brij-35. Prior to the assay, proMMP-9 (CALBIOCHEM) was incubated either with the recombinant fusion protein or control protein in the enzyme activation buffer containing 50 mM Tris-HCl, pH 7.5, 100 mM NaCl and 1 mM $CaCl_2$. The enzymatic reaction was terminated by the addition of 3.5 mM EDTA and 0.03% bovine serum albumin. The reaction sample was subsequently precipitated with 0.06% tannic acid and 1% trichloroacetic acid (TCA). The radioactivity in the TCA soluble fraction was determined by a β-scintillation counter which gives a measure of the enzymatic activity of MMP-9. The peptide of SEQ ID NO:1 inhibited MMP-9 activity in a dose-dependent manner, as shown in FIG. 2. In addition, MMP-3 dependent activation of MMP was inhibited in a dose-dependent manner, as in FIG. 3.

What is claimed is:

1. An isolated peptide comprising the amino acid sequence shown in SEQ ID NO: 1.

2. A peptide with at least 60% homology to the peptide in claim 1, wherein the peptide with at least 60% homology to the peptide in claim 1 inhibits MMP-9 activity in an in vitro assay.

3. A fusion protein comprising the peptide of claim 1, linked in-frame to maltose-binding protein.

* * * * *